(12) United States Patent
Morijiri et al.

(10) Patent No.: US 6,458,917 B2
(45) Date of Patent: *Oct. 1, 2002

(54) POLYMERIZABLE COMPOSITION

(75) Inventors: Hiroyuki Morijiri; Seiichi Kobayashi; Koju Okazaki; Chitoshi Shimakawa; Akinori Ryu; Yoshinobu Kanemura, all of Fukuoka (JP)

(73) Assignee: Mitsui Chemicals, Inc. (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/918,549

(22) Filed: Aug. 1, 2001

Related U.S. Application Data

(60) Continuation of application No. 09/745,448, filed on Dec. 26, 2000, now Pat. No. 6,300,464, which is a division of application No. 09/263,483, filed on Mar. 8, 1999, now Pat. No. 6,204,311.

(30) Foreign Application Priority Data

Mar. 13, 1998 (JP) .............................................. 10-63402
Feb. 8, 1999 (JP) .............................................. 11-30246

(51) Int. Cl.$^7$ .............................................. C08G 75/08
(52) U.S. Cl. ........................ 528/373; 523/427; 523/428; 252/182.17; 252/183.11
(58) Field of Search ........................ 252/182.17, 183.11; 523/427, 428; 528/373

(56) References Cited

U.S. PATENT DOCUMENTS 3,467,558 A     9/1969   Wernette et al.
3,856,933 A    12/1974   Jankowiak et al.
5,807,975 A     9/1998   Amagai et al.
5,945,504 A     8/1999   Amagai et al.

FOREIGN PATENT DOCUMENTS

| | | |
|---|---|---|
| EP | 0 921 417 A2 | 6/1999 |
| GB | 2111053 | 6/1983 |
| JP | 50-022554 | 7/1975 |
| JP | 9-71580 | 3/1997 |
| JP | 9-110979 | 4/1997 |
| JP | 9-255781 | 9/1997 |
| JP | 10-298287 | 11/1998 |

*Primary Examiner*—Kriellion A. Sanders
(74) *Attorney, Agent, or Firm*—Burns, Doane, Swecker & Mathis, L.L.P.

(57) ABSTRACT

An optical resin prepared by curing a polymerizable composition comprising a (thio)epoxy compound having at least one intramolecular disulfide bond exhibits a considerably high refractive index while maintaining good optical properties and a high Abbe number. In addition, the above polymerizable composition to which is added primary and/or secondary amines as an yellowing inhibitor in a proportion of 0.001 to 0.5 of the total molar number of $NH_2$ and NH groups in the amines to the total molar number of thioepoxy and epoxy groups in the (thio)epoxy compound having at least one intramolecular disulfide bond, can provide a transparent resin in which yellowing and reduction in heat resistance associated therewith are adequately prevented while maintaining a high refractive index.

10 Claims, No Drawings

POLYMERIZABLE COMPOSITION

This application is a continuation of application No. Ser. 09/745,448, filed on Dec. 26, 2000 now U.S. Pat. No. 6,300,464 which is a divisional of application No. 09/263,483, filed on Mar. 8. 1999, now U.S. Pat. No. 6,204,311, and issued on Mar. 20, 2001.

BACKGROUND OF THE INVENTION

1. Field of the Invention

This invention relates to a (thio)epoxy compound suitably used in the field of resins such as optical materials including plastic lenses, prisms, optical fibers, information recording media and light emitting diodes which are required to have a high refractive index and a high transparency, as well as resins therefrom.

This invention also relates to a polymerizable composition suitably used as a starting material for a plastic lens for eyeglasses.

2. Description of the Related Art

A plastic lens is lighter and less brittle than an inorganic lens, and dyeable, which has been therefore rapidly prevailing in the areas of optical devices such as a lens of eyeglasses and a camera lens. Such a plastic lens is required to exhibit optical properties including a high refractive index and a high Abbe number and physical properties including high heat resistance and a low specific gravity.

Among these, high heat resistance and a low specific gravity have been considerably achieved by a current plastic lens with a high refractive index. Currently, the resins which may be widely used for these applications, include those prepared by radical polymerization of diethylene glycol bis(allylcarbonate) (referred to as "D.A.C."). These resins have various features such as excellent impact resistance, lightness, excellent dye-affinity, and good processability including machinability and abradability. These resins, however, have a low refractive index (nd) of about 1.50, leading to a lens with thick center and margin. Thus, there is a need for a resin for a lens with a higher refractive index.

Resins with a higher refractive index than D.A.C. resin are known; for example, polythiourethane resins (e.g., JP-A 63-46213); sulfur-containing O-(meth)acrylate resins (e.g., JP-A 1-128966, 3-217412 and 4-16141); and thio(meth) acrylate resins (e.g., JP-A 63-188660 and JP-B 3-59060), in which sulfur atoms are introduced. A polythiourethane resin is well-balanced in its properties, that is, having suitable properties such as a high refractive index and good impact resistance.

A refractive index and an Abbe number are, however, conflicting properties; as the refractive index increases, the Abbe number decreases. It is, therefore, quite difficult to simultaneously improve these properties. Thus, it has been intensively investigated to achieve a high refractive index, preventing an Abbe number from being decreased.

Most typical suggestions of these attempts are processes using a (thio)epoxy compound as described in JP-As 9-110979, 9-71580 and 9-255781.

According to the processes, a high refractive index can be achieved while maintaining a relatively high Abbe number. A resin prepared according to these processes exhibits a refractive index of nd=about 1.70. Thus, it cannot be considered to meet the need for an improved refractive index sufficient to make a margin of an eyeglass significantly thinner while maintaining a high Abbe number, compared with a commercially available common lens with nd=1.67.

An thioepoxy resin prepared from an thioepoxy compound tends to turn yellow during heating in a secondary process, long-term storage or its use. Such yellowing may cause tone alteration of an eyeglass which is required to be fashionable. Thus, it may not meet the needs of routine users of eyeglasses. A procedure for solving the problem has been suggested in, e.g., JP-A 10-298287, where athiol compound is added to an thioepoxy compound to prevent yellowing. Although such a process can prevent yellowing, addition of a thiol compound, especially a mono- or bis-functional thiol, may cause significant deterioration of heat resistance, resulting in a lens which cannot give sufficient properties for an application requiring higher heat resistance.

SUMMARY OF THE INVENTION

An objective of this invention is to provide a polymerizable composition which can be used to prepare a resin having a very high refractive index and a high transparency, specifically having nd of 1.71 or higher, maintaining a high Abbe number.

Another objective of this invention is to provide a polymerizable composition which can give a resin maintaining a high refractive index and a high heat resistance, and which can prevent yellowing.

The inventors have intensely investigated to solve the above problems and finally have found that a higher refractive index can be provided by using a (thio)epoxy compound having at least one intramolecular disulfide bond which has been believed to be unstable (e.g., Reld. E. E., Organic Chemistry of Bivalent Sulfur Vol.3).

Specifically, one aspect of this invention is a polymerizable composition comprising a (thio)epoxy compound having at least one intramolecular disulfide bond. We have found that the polymerizable composition can be cured to give a resin with a high refractive index of nd=1.71 or higher.

There has been no information for physical properties or other characteristics of a polysulfide polymer prepared by curing a polymerizable composition containing a (thio) epoxy compound comprising at least one intramolecular disulfide bond.

The second aspect of this invention is a polymerizable composition comprising one or more compounds selected from the group of compounds having at least one $NH_2$ group and/or at least one NH group per a molecule as a yellowing inhibitor, having a total molar ratio of 0.001 to 0.5 of $NH_2$ and NH groups in the inhibitor to thioepoxy and epoxy groups in the (thio)epoxy compound comprising at least one intramolecular disulfide bond. We have found that a resin from the second polymerizable composition of this invention exhibits a high refractive index and a high Abbe number without heat resistance reduction or yellowing.

DETAILED DESCRIPTION OF THE PREFERRED EMBODIMENTS

The first aspect of this invention will be described in detail.

A polymerizable composition comprising a (thio)epoxy compound having at least one intramolecular disulfide bond according to the first aspect of this invention contains at least one epoxy or thioepoxy compound having a disulfide bond and an epoxy or thioepoxy group. The composition may contain inorganic and/or organic compounds including polyether or polysulfide oligomers such as dimers, trimers and tetramers thereof, inorganic and organic acids added as a polymerization retarder, solvents or other by-products as long as they are not harmful.

In the specification, the term "(thio)epoxy" means thioepoxy or epoxy. Thioepoxy is represented by the following structure:

A (thio)epoxy compound having at least one intramolecular disulfide bond includes (thio)epoxy compound having one intramolecular disulfide bond such as bis(2,3-epoxypropyl) disulfide and bis(2,3-epithiopropyl) disulfide; (thio)epoxy compounds having two or more intramolecular disulfide bonds such as bis(2,3-epithiopropyldithio) methane, bis(2,3-epithiopropyldithio)ethane, bis(6,7-epithio-3,4-dithiaheptane) sulfide, 1,4-dithian-2,5-bis(2,3-epithiopropyldithiomethyl, 1,3-bis(2,3-epithiopropyldithiomethyl)benzene, 1,6-bis(2,3-epithiopropyldithio)-2-(2,3-epithiopropyldithioethylthio)-4-thiahexane and 1,2,3-tris(2,3-epithiopropyldithio)propane. Among the compounds, (thio) epoxy compounds having one intramolecular disulfide bond represented by formula (1) are preferred. Besides the process described in the document, bis(2,3-epithiopropyl) disulfide can be prepared by reacting bis(2,3-epoxypropyl) disulfide with a sulfurating agent such as a thiocyanate, thiourea, triphenylphosphine sulfide and 3-methylbenzothiazol-2-thione, preferably a thiocyanate and thiourea.

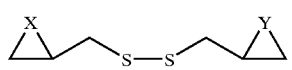

(1)

wherein X and Y are independently oxygen or sulfur and may be different or the same.

A most preferred (thio)epoxy compound having at least one intramolecular disulfide bond is bis(2,3-epithiopropyl) disulfide.

The (thio)epoxy compound having at least one intramolecular disulfide bond may be used to improve a refractive index of a resin prepared by curing a polymerizable composition comprising the (thio)epoxy compound.

A polymerizable composition comprising a (thio)epoxy compound having at least one intramolecular disulfide bond according to the first aspect of this invention may contain resin modifiers for mainly improving resin properties, e.g., adjusting optical properties such as a refractive index; and physical properties such as impact resistance and a specific gravity, as well as handling properties such as the viscosity of the composition.

Resin modifiers which may be used include (thio)epoxy compounds other than those contained in the (thio)epoxy compound having at least one intramolecular disulfide bond according to the first aspect of this invention, thiols, organic mercapto acids, organic acids and acid anhydrides, amino acids, mercaptoamines, amines and olefins including (meth) acrylates.

Specific examples of the thioepoxy compound as a modifier are, but not limited to, linear aliphatic 2,3-epithiopropylthio compounds such as bis(2,3-epithiopropyl) sulfide, bis(2,3-epithiopropyl-thio)methane, 1,2-bis(2,3-epithiopropylthio)ethane, 1,2-bis(2,3-epithiopropylthio) propane, 1,3-bis(2,3-epithiopropylthio)propane, 1,3-bis(2,3-epithiopropylthio)-2-methylpropane, 1,4-bis(2,3-epithiopropylthio)butane, 1,4-bis(2,3-epithiopropylthio)-2-methylbutane, 1,3-bis(2,3-epithiopropylthio)butane, 1,5-bis(2,3-epithiopropylthio)pentane, 1,5-bis(2,3-epithiopropylthio)-2-methylpentane, 1,5-bis(2,3-epithiopropylthio)-3-thiapentane, 1,6-bis(2,3-epithiopropylthio)hexane, 1,6-bis(2,3-epithiopropylthio)-2-methylhexane, 1,8-bis(2,3-epithiopropylthio)-3,6-dithiaoctane, 1,2,3-tris(2,3-epithiopropylthio)propane, 2,2-bis(2,3-epithiopropylthio)-1,3-bis(2,3-epithiopropylthiomethyl)propane, 2,2-bis(2,3-epithiopropylthiomethyl)-1-(2,3-epithiopropylthio)butane, 1,5-bis(2,3-epithiopropyl-thio)-2-(2,3-epithiopropylthiomethyl)-3-thia-pentane, 1,5-bis(2,3-epithiopropylthio)-2,4-bis(2,3-epithiopropylthiomethyl)-3-thiapentane, 1-(2,3-epithiopropylthio)-2,2-bis(2,3-epithiopropylthiomethyl)-4-thiahexane, 1,5,6-tris(2,3-epithiopropylthio)-4-(2,3-epithiopropylthio-methyl)-3-thiahexane, 1,8-bis(2,3-epithiopropyl-thio)-4-(2,3-epithiopropylthiomethyl)-3,6-dithia-octane, 1,8-bis(2,3-epithiopropylthio)-4,5-bis-(2,3-epithiopropylthiomethyl)-3,6-dithiaoctane, 1,8-bis(2,3-epithiopropylthio)-4,4-bis(2,3-epithiopropylthiomethyl)-3,6-dithiaoctane, 1,8-bis-(2,3-epithiopropylthio)-2,5-bis(2,3-epithiopropylthiomethyl)-3,6-dithiaoctane, 1,8-bis(2,3-epithiopropylthio)-2,4,5-tris(2,3-epithiopropyl-thiomethyl)-3,6-dithiaoctane, 1,1,1-tris{[2-(2,3-epithiopropylthio)ethyl]thiomethyl}-2-(2,3-epithiopropylthio)ethane, 1,1,2,2-tetrakis{[2-(2,3-epithiopropylthio)ethyl]thiomethyl}ethane, 1,11-bis(2,3-epithiopropylthio)-4,8-bis(2,3-epithiopropylthiomethyl)-3,6,9-trithiaundecane, 1,11-bis(2,3-epithiopropylthio)-4,7-bis (2,3-epithiopropylthiomethyl)-3,6,9-trithiaundecane and 1,11-bis(2,3-epithiopropylthio)-5,7-bis(2,3-epithiopropylthiomethyl)-3,6,9-trithiaundecane; alicyclic 2,3-epithiopropylthio compounds such as 1,3-bis(2,3-epithiopropylthio)cyclohexane, 1,4-bis(2,3-epithiopropylthio)cyclohexane, 1,3-bis(2,3-epithiopropylthiomethyl)cyclohexane, 1,4-bis(2,3-epithiopropylthiomethyl)cyclohexane, 2,5-bis(2,3-epithiopropylthiomethyl)-1,4-dithiane, 2,5-bis{[2-(2,3-epithiopropylthio)ethyl]-thiomethyl}-1,4-dithiane and 2,5-bis(2,3-epithio-propylthiomethyl)-2,5-dimethyl-1,4-dithiane; aromatic 2,3-epithiopropylthio compounds such as 1,2-bis(2,3-epithiopropylthio)benzene, 1,3-bis-(2,3-epithiopropylthio)benzene, 1,4-bis(2,3-epithiopropylthio) benzene, 1,2-bis(2,3-epithiopropylthiomethyl)benzene, 1,3-bis(2,3-epithiopropylthiomethyl)benzene, 1,4-bis(2,3-epithiopropylthiomethyl)benzene, bis[4-(2,3-epithiopropylthio)phenyl]methane, 2,2-bis[4-(2,3-epithiopropylthio)phenyl]propane, bis[4-(2,3-epithiopropylthio)phenyl] sulfide, bis[4-(2,3-epithiopropylthio)phenyl] sulfone and 4,4'-bis(2,3-epithiopropylthio)biphenyl; monofunctional epithio compounds such as ethylene sulfide and propylene sulfide; and epithio compounds comprising a mercapto group such as 3-mercaptopropylene sulfide and 4-mercaptobutene sulfide.

Specific epoxy compounds which may be used include, but are not limited to, phenolic epoxy compounds prepared by condensation of an epihalohydrin with a polyphenol including bisphenol-A glycidyl ether; alcoholic epoxy compounds prepared by condensation of an epihalohydrin with a polyalcohol including hydrogenated bisphenol-A glycidyl ether; glycidyl ester epoxy compounds prepared by condensation of an epihalohydrin with an organic polyacid derivative including 3,4-epoxycyclohexylmethyl-3',4'-epoxycyclohexane carboxylate and diglycidyl 1,2-hexahydrophthalate; amino epoxy compounds prepared by condensation of an epihalohydrin with a secondary amine; and aliphatic polyepoxy compounds such as vinylcyclohexene diepoxide.

Specific thiols which may be used include, but are not limited to, aliphatic thiols such as methyl mercaptan, ethyl mercaptan, 1,2-ethanedithiol, 1,2-propanedithiol, 1,3-propanedithiol, 2,2-propanedithiol, 1,4-butanedithiol, 1,2,3-trimercaptopropane, tetrakis(mercaptomethyl)-methane, 1,2-dimercaptocyclohexane, bis(2-mercaptoethyl) sulfide, 2,3-dimercapto-1-propanol, ethyleneglycol bis(3-mercaptopropionate), diethyleneglycol bis(3-mercaptopropionate), diethyleneglycol bis(2-mercaptoglycolate), pentaerythritol tetrakis(2-mercaptothioglycolate), pentaerythritol tetrakis(3-mercaptopropionate), trimethylolpropane tris(2-mercaptothioglycolate), trimethylolpropane tris(3-mercaptopropionate), 1,1,1-trimethylmercaptoethane, 1,1,1-trimethylmercaptopropane, 2,5-dimercaptomethylthiophane, 4-mercaptomethyl-1,8-dimercapto-3,6-dithiaoctane, 2,5-dimercaptomethyl-1,4-dithiane, 2,5-bis[(2-mercaptoethyl)thiomethyl]-1,4-dithiane, 1,3-cyclohexanedithiol, 1,4-cyclohexanedithiol, 4,8-dimercaptomethyl-1,11-dimercapto-3,6,9-trithiaundecane, 4,7-dimercaptomethyl-1,11-dimercapto-3,6,9-trithiaundecane and 5,7-dimercaptomethyl-1,11-dimercapto-3,6,9-trithiaundecane; and aromatic thiols such as benzylthiol, thiophenol, 1,2-dimercaptobenzene, 1,3-dimercaptobenzene, 1,4-dimercaptobenzene, 1,2-bis(mercaptomethyl)-benzene, 1,3-bis(mercaptomethyl)benzene, 1,4-bis(mercaptomethyl)benzene, 2,2'-dimercaptobiphenyl, 4,4'-dimercaptobiphenyl, bis(4-mercaptophenyl)methane, bis(4-mercaptophenyl) sulfide, bis(4-mercaptophenyl) sulfone, 2,2-bis(4-mercaptophenyl) propane, 1,2,3-trimercaptobenzene, 1,2,4-trimercaptobenzene and 1,2,5-trimercaptobenzene.

Organic mercapto acids which may be used include, but are not limited to, thioglycolic acid, 3-mercaptopropionic acid, thioacetic acid, thiolactic acid, thiomalic acid and thiosalicylic acid. Organic acids and their anhydrides which may be used include, but are not limited to, the above polymerization retarders as well as thiodiglycolic acid, thiodipropionic acid, dithiodipropionic acid, phthalic anhydride, hexahydrophthalic anhydride, methylhexahydrophthalic anhydride, methyltetrahydrophthalic anhydride, methylnorbornenoic anhydride, methylnorbornanoic anhydride, maleic anhydride, trimellitic anhydride and pyromellitic dianhydride.

Olefins which may be used include, but are not limited to, (meth)acrylates such as benzyl acrylate, benzyl methacrylate, butoxyethyl acrylate, butoxymethyl methacrylate, cyclohexyl acrylate, cyclohexyl methacrylate, 2-hydroxyethyl acrylate, 2-hydroxyethyl methacrylate, glycidyl acrylate, glycidyl methacrylate, phenoxyethyl acrylate, phenoxyethyl methacrylate, phenyl methacrylate, 3-phenoxy-2-hydroxypropyl acrylate, ethyleneglycol diacrylate, ethyleneglycol dimethacrylate, diethyleneglycol diacrylate, diethyleneglycol dimethacrylate, triethyleneglycol diacrylate, triethyleneglycol dimethacrylate, tetraethyleneglycol diacrylate, tetraethyleneglycol dimethacrylate, polyethyleneglycol diacrylate, polyethyleneglycol dimethacrylate, neopentylglycol diacrylate, neopentylglycol dimethacrylate, ethyleneglycolbisglycidyl diacrylate, ethyleneglycolbisglycidyl dimethacrylate, bisphenol-A diacrylate, bisphenol-A dimethacrylate, 2,2-bis(4-acryloxyethoxyphenyl)propane, 2,2-bis(4-methacryloxyethoxyphenyl)propane, 2,2-bis(4-acryloxydiethoxyphenyl)propane, 2,2-bis(4-methacryloxydiethoxyphenyl)propane, bisphenol-F diacrylate, bisphenol-F dimethacrylate, 1,1-bis(4-acryloxyethoxyphenyl)methane, 1,1-bis(4-methacryloxyethoxyphenyl)methane, 1,1-bis(4-acryloxydiethoxyphenyl)methane, 1,1-bis(4-methacryloxydiethoxyphenyl)methane, dimethyloltricyclodecane diacrylate, trimethylolpropane triacrylate, trimethylolpropane trimethacrylate, glycerol diacrylate, glycerol dimethacrylate, pentaerythritol triacrylate, pentaerythritol tetraacrylate, pentaerythritol tetramethacrylate, methylthio acrylate, methylthio methacrylate, phenylthio acrylate, benzylthio methacrylate, xylenedithiol diacrylate, xylenedithiol dimethacrylate, mercaptoethylsulfide diacrylate and mercaptoethylsulfide dimethacrylate; allyl compounds such as allyl glycidyl ether, diallyl phthalate, diallyl terephthalate, diallyl isophthalate, diallyl carbonate and diethyleneglycol-bisallyl carbonate; vinyl compounds such as styrene, chlorostyrene, methylstyrene, bromostyrene, dibromostyrene, divinylbenzene and 3,9-divinyl-spiro-bis(m-dioxane); and diisopropenylbenzene.

These resin modifiers may be used alone or in combination of two or more thereof.

Curing catalysts which may be used in the first aspect of this invention may be typically tertiary amines, phosphines, Lewis acids, radical polymerization catalysts and cationic polymerization catalysts.

The preferable curing catalysts include, but are not limited to, aliphatic and aromatic tertiary amines such as triethylamine, tri-n-butylamine, tri-n-hexylamine, N,N-diisopropylethylamine, triethylenediamine, triphenylamine, N,N-dimethylethanolamine, N,N-diethylethanolamine, N,N-dibutylethanolamine, triethanolamine, N-ethyldiethanolamine, N,N-dimethylbenzylamine, N,N-diethylbenzylamine, tribenzylamine, N-methyldibenzylamine, N,N-dimethylcyclohexylamine, N,N-diethylcyclohexylamine,N,N-dimethylbutylamine, N-methyldicyclohexylamine, N-methylmorpholine, N-isopropylmorpholine, pyridine, quinoline, N,N-dimethylaniline, N,N-diethylaniline, α, β- or γ-picoline, ,2'-dipyridyl, 1,4-dimethylpiperazine, dicyandiamide, tetramethylethylenediamine, hexamethylenetetramine, 1,8-diazabicyclo[5.4.0]-7-undecene and 2,4,6-tris(N,N-dimethylaminomethyl)phenol; phosphines such as trimethylphosphine, triethylphosphine, tri-n-propylphosphine, triisopropylphosphine, tri-n-butylphosphine, triphenylphosphine, tribenzylphosphine, 1,2-bis(diphenylphosphino)ethane and 1,2-bis(dimethylphosphino)ethane; Lewis acids such as dimethyltin dichloride, dibutyltin dichloride, dibutyltin dilaurate, tetrachlorotin, dibutyltin oxide, zinc chloride, zinc acetylacetonate, aluminum chloride, aluminum fluoride, triphenylaluminum, titanium tetrachloride and calcium acetate; radical polymerization catalysts such as 2,2'-azobis(2-cyclopropylpropionitrile), 2,2'-azobis(4-methoxy-2,4-dimethylvaleronitrile), 2,2'-azobis(2,4-dimethylvaleronitrile), t-butylperoxy-2-ethyl hexanoate, n-butyl-4,4'-bis(t-butylperoxy)valerate and t-butyl peroxybenzoate; and cationic polymerization catalysts such as diphenyliodonium hexafluorophosphate, diphenyliodonium hexafluoroarsenate, diphenyliodonium hexafluoroantimony, triphenylsulfonium tetrafluoroborate, triphenylsulfonium hexafluorophosphate and triphenylsulfonium hexafluoroarsenate.

These curing catalysts may be used alone or in combination of two or more thereof.

A curing catalyst may be preferably added in a proportion of 0.001 to 10 wt %, more preferably 0.01 to 5 wt % to the total amount of the polymerizable composition comprising a (thio)epoxy compound. If the proportion is less than 0.001 wt %, polymerization may be insufficient due to a too small effect of the catalyst. On the other hand, the catalyst may be contained in a proportion of more than 10 wt %, but it may cause problems such as a shorter pot life and deterioration in transparency, optical properties or weatherproof properties.

A typical polymerization process for preparing the resin according to the first aspect of this invention (e.g., a plastic lens) is casting polymerization. Specifically, a polymerizable composition comprising a (thio)epoxy compound and a curing catalyst, which may be also referred to as a monomer mixture, is poured between molds held by a fixing means such as a gasket and tapes, during which some treatments such as defoaming may be, if necessary, conducted.

Then, it may be subject to curing by heating in a heating apparatus such as an oven or in water, and then a polymerization product may be removed from the mold.

A polymerization method or polymerization conditions for preparing a resin according to the first aspect of this invention cannot be generalized since they depend on the amounts and types of ingredients such as curing catalysts as well as types and proportions of monomers.

Heat curing conditions in the mold for a polymerizable composition according the first aspect of this invention significantly vary depending on various factors such as a type of a composition comprising a (thio)epoxy compound, a type of a curing catalyst and the shape of the mold and therefore cannot be specifically limited, but the composition may be typically cured at −50 to 200° C. for 1 to 100 hours. It may be cured keeping or gradually raising the temperature within a range of 10° C. to 150° C. for 1 to 80 hours, providing good results.

In addition, a composition comprising a (thio)epoxy compound having at least one intramolecular disulfide bond, especially a (thio)epoxy compound having an intramolecular disulfide bond, may be cured in a reduced time by UV irradiation, where a curing catalyst such as a radical polymerization catalyst may be necessary.

For molding a resin according to the first aspect of this invention, a variety of substances such as chain extenders, crosslinking agents, photostabilizers, UV absorbents, antioxidants, anti-coloring agents, dyes, fillers and internal mold release agents, may be added, depending on the purpose, as in the known molding methods.

The resin, which has been removed from the mold, may be, if necessary, annealed.

A resin obtained by curing a polymerizable composition comprising a (thio)epoxy compound having at least one intramolecular disulfide bond according to the first aspect of this invention has a high refractive index, a reduced dispersibility and a high thermal resistance, especially an extremely high refractive index. It is a transparent resin having a refractive index of preferably $nd \geq 1.71$, more preferably $nd \geq 1.72$, most preferably $nd \geq 1.73$. Furthermore, the resin of this invention can be formed in various forms by altering a mold in the casting polymerization, and be thus used as optical device materials for an eyeglass lens, a camera lens and a light emitting diode (LED), as well as a transparent resin for a variety of applications. In particular, it is suitable for an optical device material for an eyeglass lens and a camera lens.

Furthermore, a lens from the resin according to the first aspect of this invention may be, if necessary, subject to physical or chemical post-treatments such as surface abrasion, antistatic treatment, hard coating, non-reflection coating and dyeing, for improvements such as prevention of reflection; improvement in hardness, abrasion resistance or chemical resistance; and impartation of antifog or cosmetic property.

Next, the second aspect of this invention will be described in detail.

JP-As 9-110979, 9-71580, 9-255781 and 10-298287 describing thioepoxy resins list primary and secondary amines corresponding to Compound (b) according to the second aspect of this invention as a curing catalyst, but they have disclosed only hydrogenated 4,4'-diaminodiphenylmethane in their examples and comparative examples. In our investigation, when hydrogenated 4,4'-diaminodiphenylmethane was used as a curing catalyst, a reaction mixture became cloudy and lost transparency due to local polymerization immediately after adding 4,4'-diaminodiphenylmethane to an thioepoxy compound. In addition, polymerization could not be completed even after heating and thus a satisfactory resin was not obtained. Among the other amines listed except tertiary amines, primary and secondary amines corresponding to a compound having an amino group and/or an imino group of this invention did not exhibit satisfactory effects as a curing catalyst, so that the polymerization was not completed and a viscous liquid or a gummy resin was provided. Thus, we have found that primary and secondary amines can be used not as a curing catalyst for an thioepoxy resin, but as an yellowing inhibitor which may prevent deterioration in heat resistance.

In the second aspect of this invention, the composition has a proportion of 0.001 to 0.5, preferably equal to or more 0.01 and less than 0.3 of the total molar number of $NH_2$ and NH groups in the above primary and secondary amines (referred to as Compound (b)) to the total molar number of thioepoxy and epoxy groups in a (thio)epoxy compound having at least one intramolecular disulfide bond (referred to as Compound (a)).

If the total molar ratio is more than 0.5, a resulting resin after polymerization has reduced heat resistance and a lower refractive index. If the ratio is less than. 0.001, yellowing cannot be adequately prevented as intended in the second aspect of this invention.

A polymerizable composition according to the second aspect of this invention comprises Compounds (a) and (b), and may contain inorganic and/or organic compounds including polyether or polysulfide oligomers such as dimers, trimers and tetramers thereof, inorganic and organic acids added as a polymerization retarder, solvents or other by-products as long as they are not harmful.

A polymerizable composition according to the second aspect of this invention may contain resin modifiers for mainly improving resin properties, e.g., adjusting optical properties such as a refractive index; and physical properties such as impact resistance and a specific gravity, as well as improving handling properties as the viscosity of the composition.

Resin modifiers which may be used are as described above.

Preferable examples of Compound (b) in the second aspect of this invention are, but not limited to, (1) monofunctional primary amines such as ethylamine, n-propylamine, isopropylamine, n-butylamine, sec-butylamine, tert-butylamine, pentylamine, hexylamine, heptylamine, octylamine, decylamine, laurylamine, myristylamine, 3-pentylamine, 2-ethylhexylamine, 1,2-dimethylhexylamine, allylamine, aminomethylbicycloheptane, cyclopentylamine, cyclohexylamine, 2,3-dimethylcyclohexylamine, aminomethylcyclohexane, aniline, benzylamine, phenethylamine, 2-, 3- or 4-methylbenzylamine, o-, m- or p-methylaniline, o-, m- or p-ethylaniline, aminomorpholine, naphthylamine, furfurylamine, a-aminodiphenylmethane, toluidine, aminopyridine, aminophenol, aminoethanol, 1-aminopropanol, 2-aminopropanol, aminobutanol, aminopentanol, aminohexanol, methoxyethylamine, 2-(2-aminoethoxy) ethanol, 3-ethoxypropylamine, 3-propoxypropylamine, 3-butoxypropylamine, 3-isopropoxypropylamine, 3-isobutoxypropylamine and 2,2-diethoxyethylamine; and primary polyamines such as ethylenediamine, 1,2-or 1,3-diaminopropane, 1,2-, 1,3- or 1,4-diaminobutane, 1,5-diaminopentane, 1,6-diaminohexane, 1,7-diaminoheptane, 1,8-diaminooctane, 1,10-diaminodecane, 1,2-, 1,3- or 1,4-diaminocyclohexane, o-, m- or p-diaminobenzene, 3,4- or 4,4'-diaminobenzophenone, 3,4- or 4,4'-diaminodiphenyl ether, 4,4'-diaminodiphenylmethane, 4,4'-diaminodiphenyl sulfide, 3,3'- or 4,4'-diaminodiphenyl sulfone, 2,7-diaminofluorene, 1,5-, 1,8- or 2,3-diaminonaphthalene, 2,3-, 2,6- or 3,4-diaminopyridine, 2,4- or 2,6-diaminotoluene, m- or p-xylylenediamine, isophoronediamine, diaminomethylbicycloheptane, 1,3- or 1,4-diaminomethylcyclohexane, 2- or 4-aminopiperidine, 2- or 4-aminomethylpiperidine, 2- or 4-aminoethylpiperidine, N-aminoethylmorpholine and N-aminopropylmorpholine;

(2) monofunctional secondary amines such as diethylamine, dipropylamine, di-n-butylamine, di-sec-butylamine, diisobutylamine, di-n-pentylamine, di-3-pentylamine, dihexylamine, dioctylamine, di(2-ethylhexyl)amine, methylhexylamine, diallylamine, N-methylallylamine, piperidine, pyrrolidine, diphenylamine, N-methylphenylamine, N-ethylphenylamine, dibenzylamine, N-methylbenzylamine, N-ethylbenzylamine, dicyclohexylamine, N-methylaniline, N-ethylaniline, dinaphthylamine, 1-methylpiperazine and morpholine; and secondary polyamines such as N,N'-dimethylethylenediamine, N,N'-dimethyl-1,2-diaminopropane, N,N'-dimethyl-1,3-diaminopropane, N,N'-dimethyl-1,2-diaminobutane, N,N'-dimethyl-1,3-diaminobutane, N,N'-dimethyl-1,4-diaminobutane, N,N'-dimethyl-1,5-diaminopentane, N,N'-dimethyl-1,6-diaminohexane, N,N'-dimethyl-1,7-diaminoheptane, N,N'-diethylethylenediamine, N,N'-diethyl-1,2-diaminopropane, N,N'-diethyl-1,3-diaminopropane, N,N'-diethyl-1,2-diaminobutane, N,N'-diethyl-1,3-diaminobutane, N,N'-diethyl-1,4-diaminobutane, N,N'-diethyl-1,5-diaminopentane, N,N'-diethyl-1,6-diaminohexane, N,N'-diethyl-1,7-diaminoheptane, piperazine, 2-methylpiperazine, 2,5-dimethylpiperazine, 2,6-dimethylpiperazine, homopiperazine, 1,1-di-(4-piperidyl)methane, 1,2-di-(4-piperidyl)ethane, 1,3-di-(4-piperidyl)propane, 1,4-di-(4-piperidyl)butane and tetramethylguanidine. These may be used alone or in combination of two or more thereof. More preferable compounds are benzylamine and piperazines.

A polymerizable composition according to the second aspect of this invention may be cured by heating or being left at an ambient temperature in the presence or absence of a curing catalyst, to provide a resin. It may be preferable to use a curing catalyst since curing may not proceed adequately or at all in the absence of the catalyst. Typical curing catalysts which may be used for the second aspect of this invention include amines other than Compound (b) in the second aspect of this invention, phosphines, Lewis acids, radical polymerization catalysts and cation polymerization catalysts as described in terms of the first aspect of this invention.

A curing catalyst may be preferably added in a proportion of 0.001 to 10 wt %, more preferably 0.01 to 1 wt % to the total amount of the polymerizable composition comprising Compound (a) having an epoxy or thioepoxy group. If its proportion is less than 0.001 wt %, polymerization may be insufficient due to a too small effect of the catalyst. On the other hand, the catalyst may be contained in a proportion of more than 10 wt %, but it may cause problems such as a shorter pot life and deterioration in transparency, optical properties or weatherproof properties.

A typical polymerization process for preparing the resin according to the second aspect of this invention(e.g., a plastic lens) is casting polymerization. Specifically, a polymerizable composition according to the second aspect of this invention, after mixing, if necessary, with a curing catalyst and/or a resin modifier, is poured between molds held by a fixing means such as a gasket and tapes. Before or after pouring, some treatments such as defoaming may be, if necessary, conducted.

Then, it may be subject to curing by heating in a heating apparatus such as an oven or in water, and then a polymerization product may be removed from the mold.

A polymerization method and polymerization conditions for preparing a resin according to the second aspect of this invention cannot be generalized since they depend on the amounts and types of ingredients such as curing catalysts as well as types and proportions of monomers.

Heat curing conditions for a polymerizable composition according the second aspect of this invention poured into the mold significantly vary depending on various factors such as Compounds (a) and (b) in the second aspect of this invention, a type of a resin modifier, a type of a curing catalyst and the shape of the mold and therefore cannot be specifically limited, but the composition may be typically cured at −50 to 200° C. for 1 to 100 hours.

It may be cured keeping or gradually raising the temperature within a range of 10° C. to 150° C. for 1 to 80 hours, providing good results.

In addition, the polymerizable composition according to the second aspect of this invention may be cured in a reduced time by UV irradiation, where a curing catalyst such as a radical polymerization catalyst may be added.

For molding a resin according to the second aspect of this invention, a variety of substances such as chain extenders, crosslinking agents, photostabilizers, UV absorbents, antioxidants, anti-coloring agents other than those in the second aspect of this invention, dyes, fillers, internal and external mold release agents, internal and external adherence improver and compounds having a hydroxy group as a dye-affinity improver may be added, depending on the purpose, as in the known molding methods.

The resin, which has been removed from the mold, may be, if necessary, annealed. Furthermore, the resin of the second aspect of this invention can be formed in various forms by altering a mold in the casting polymerization, and be thus used as an optical material for an eyeglass lens, a camera lens and a light emitting diode (LED), as well as a transparent resin for a variety of applications. In particular, it is suitable for an optical material for an eyeglass lens and a camera lens.

Furthermore, a lens from the optical material according to the second aspect of this invention may be, if necessary, subject to physical or chemical post-treatments such as surface abrasion, antistatic treatment, hard coating, non-reflection coating and dyeing, for improvements such as prevention of reflection; improvement in hardness, abrasion resistance or chemical resistance; and impartation of antifog or cosmetic property.

This invention will be specifically described by the following examples and preparation examples. The properties relevant to performance of a resin obtained, that is, a refractive index, an Abbe number, a specific gravity and heat resistance were evaluated as follows.

(1) A refractive index (nd) and Abbe number (vd): measured at 20° C. using a Pulfrich refractometer.

(2) Specific gravity: measured by Archimedes' method.

(3) Heat resistance: Tg was measured by TMA penetration method (load: 50 g, pinpoint: 0.5 mmφ, temperature-programming rate: 10° C./min.).

PREPARATION EXAMPLE 1
Bis(2,3-epoxypropyl) disulfide

In a reaction flask equipped with an agitator, a thermometer, a gas cylinder and a condenser were placed 190 g of epichlorohydrin (2 mol), 500 mL of methanol and 1.0 g of calcium hydroxide. Keeping the internal temperature at 0 to 5° C., into the reaction system was introduced 75 g of hydrogen sulfide gas (2.2 mol) from the gas cylinder, and then the reaction was matured at 5° C. for 3 hours.

After filtration of the reaction mixture and evaporation of methanol, the residue was distilled to give chloromercaptopropanol with a purity of 99%. In a reaction vessel were placed the chloromercaptopropanol, 1000 mL of purified water and 168 g of sodium hydrogen carbonate (2 mol). Keeping the internal temperature at 5 to 10° C., to the mixture was added portionwise 254 g of solid iodine (1 mol) over 1 hour, and then the reaction mixture was aged at 10° C. for 12 hours. After aging, the reaction mixture was filtered to give white crystals, which were then dried in vacuo.

The dried white crystals, 250 mL of methanol and 500 mL of toluene were placed in a reaction vessel. Keeping the internal temperature at 3 to 5° C., 240 g of 47 wt % sodium hydroxide (2.8 mol) was added dropwise over 1 hour, and the reaction mixture was aged for 30 min. After completion of the reaction, 100 mL of toluene was added. The organic layer was washed with water three times, dried over anhydrous magnesium sulfate and filtered. The filtrate was evaporated.

The residue was filtered to give 171 g of bis(2,3-epoxypropyl) disulfide (referred to as Compound (A)) with a purity of 96 wt % (yield after calculation based on the purity: 92%). Its elemental analysis results are shown below.

|  | C | H | O | S |
|---|---|---|---|---|
| Measured (%) | 39.0 | 5.4 | 18.5 | 37.1 |
| Calculated (%) | 40.4 | 5.7 | 17.9 | 36.0 |

PREPARATION EXAMPLE 2
Bis(2,3-epithiopropyl) disulfide (Procedure 1)

In a reaction flask equipped with an agitator, a thermometer and a condenser were placed 100 g of Compound (A) prepared as described in Preparation Example 1 with a purity of 96 wt % (0.54 mol), 100 g of thiourea (1.3 mol), 2 g of acetic acid, 250 mL of toluene and 200 mL of methanol. Keeping the internal temperature at 15° C., the mixture was stirred for 16 hours.

After completion of the reaction and then adding 150 mL of toluene, the mixture was sequentially washed with sodium chloride aq., 1% sulfuric acid and again sodium chloride aq. The organic layer was dried over anhydrous magnesium sulfate, filtered and evaporated. The residue was dissolved in 600 mL of acetonitrile and the supernatant was filtered. The filtrate was evaporated to give a residue, which was then filtered to give 77.5 g of composition of a thioepoxy compound comprising bis(2,3-epithio-propyl) disulfide (referred to as Compound (B)) in 85 wt % (yield after calculation based on the purity: 58%). Its elemental analysis results are shown below.

|  | C | H | S |
|---|---|---|---|
| Measured (%) | 32.6 | 4.6 | 62.8 |
| Calculated (%) | 34.2 | 4.8 | 61.0 |

PREPARATION EXAMPLE 3
Compound (B)(Procedure 2)

In a reaction flask equipped with an agitator, a thermometer and a condenser were placed 100 g of 2,3-dimercaptopropan-1-ol (0.8 mol) and 450 mL of dichloromethane. Keeping the internal temperature at 0° C., to the stirred mixture was added dropwise 73 g of phosphorous tribromide (0.27 mol) using a dropping funnel over 1 hour, and then the reaction mixture was aged for 1 hour. After aging, to the mixture were added 134.4 g of sodium hydrogen carbonate (1.6 mol) and 1000 mL of water. The organic layer was washed with an alkaline solution, neutralized with 35% hydrochloric acid and evaporated. The residue was distilled and 50 g of fraction was collected at 26° C./0.2 mmHg. The collected product was 3-mercapto-1,2-propylene sulfide with a purity of 99 wt % (yield after calculated based on the purity: 59%).

In a reaction vessel were placed 53 g of the distillation fraction (0.5 mol), 250 mL of toluene, 250 mL of methanol and 84 g of potassium iodide (0.5 mol). Keeping the internal temperature at −20° C., to the mixture was added portionwise 127 g of solid iodine (0.5 mol) over 1 hour, and the reaction mixture was aged for 6 hours. The mixture was worked up as described in Preparation Example 2 to give a composition of a thioepoxy compound comprising Compound (B) in 81 wt % after evaporation. Its elemental analysis results are shown below.

|  | C | H | S |
|---|---|---|---|
| Measured (%) | 32.6 | 4.8 | 62.8 |
| Calculated (%) | 34.2 | 4.8 | 61.0 |

PURIFICATION EXAMPLE 1

The crude thioepoxy compound with a purity of 85 wt % prepared as described in Preparation Example 2 (50 g) was purified by silica gel chromatography to provide 38 g of polymerizable composition comprising Compound (B) with a purity of 94 wt %.

EXAMPLE 1

To 50 g of the composition of the thioepoxy compound with a purity of 85 wt % prepared as described in Preparation Example 2 was added 0.1 g of N,N-dimethylcyclohexylamine. After defoaming for 0.4 hours under a reduced pressure, the mixture was poured into a mold template consisting of glass molds and a gasket. The mold was gradually warmed from 0° C. to 120° C. and at the temperature the mixture was polymerized for 24 hours. After completion of the polymerization, the mold was gradually cooled and the molding was removed from the mold. The physical properties of the molding (lens) are shown in Table 1.

EXAMPLE 2

Compound (B) with a purity of 94 wt % prepared as described in Purification Example 1 (30 g) was tested as described in Example 1. The physical properties of the molding (lens) are shown in Table 1.

EXAMPLE 3

Compound (B) with a purity of 94 wt % prepared as described in Purification Example 1 (30 g) was tested as described in Example 1 except that 1.5 g of bis(2-mercaptoethyl) sulfide (referred to as Compound (C)) was added to Compound (B) and N,N-dimethylcyclohexylamine was replaced with 0.06 g of N,N-dimethylbenzylamine. The physical properties of the molding (lens) are shown in Table 1.

EXAMPLE 4

Compound (B) with a purity of 94 wt % prepared as described in Purification Example 1 (30 g) was tested as described in Example 1 except that 1.5 g of 4,8-, 4,7- or 5,7-dimercaptomethyl-1,11-dimercapto-3,6,9-trithiaundecane (referred to as Compound (D)) was added to Compound (B) and 0.06 g of N,N-dimethylcyclohexylamine. The physical properties of the molding (lens) are shown in Table 1.

EXAMPLE 5

Compound (B) with a purity of 94 wt % prepared as described in Purification Example 1 (30 g) was tested as described in Example 1 except that 1.5 g of Compound (A) was added to Compound (B) and 0.06 g of N,N-diethylethanolamine was added. The physical properties of the molding (lens) are shown in Table 1.

EXAMPLE 6

Compound (B) with a purity of 94 wt % prepared as described in Purification Example 1 (30 g) was tested as described in Example 1 except that 1.5 g of cyclohexene vinyl diepoxide (referred to as Compound (E)) was added to Compound (B) and 0.06 g of N,N-dimethylcyclohexylamine was added. The physical properties of the molding (lens) are shown in Table 1.

EXAMPLE 7

Compound (B) with a purity of 94 wt % prepared as described in Purification Example 1 (30 g) was tested as described in Example 1 except that 1.5 g of 1,1-bis(4-acryloxydiethoxyphenyl)methane (referred to as Compound (F)) was added to Compound (B) and 0.06 g of N,N-dimethylcyclohexylamine was added. The physical properties of the molding (lens) are shown in Table 1.

EXAMPLE 8

Compound (B) with a purity of 94 wt % prepared as described in Purification Example 1 (30 g) was tested as described in Example 1 except that 1.5 g of divinylbenzene (referred to as Compound (G)) was added to Compound (B) and 0.06 g of N,N-dimethylcyclohexylamine was added. The physical properties of the molding (lens) are shown in Table 1.

COMPARATIVE EXAMPLE 1

Bis(2,3-epithiopropyl) sulfide with a purity of 89 wt % (referred to as Compound (H))(50 g) was tested as described in Example 5. The physical properties of the molding (lens) are shown in Table 1.

TABLE 1

| | Polymerizable Composition | Refractive Index (nd) | Abbe No. | Specific Gravity | Tg (° C.) |
|---|---|---|---|---|---|
| Exam. 1 | Compd. (B) 85% Composition | 1.737 | 33 | 1.47 | 84 |
| Exam. 2 | Compd. (B) 94% Composition | 1.740 | 33 | 1.47 | 95 |
| Exam. 3 | Compds. (B) + (C) Composition | 1.734 | 33 | 1.46 | 81 |
| Exam. 4 | Compds. (B) + (D) Composition | 1.736 | 33 | 1.46 | 88 |
| Exam. 5 | Compds. (B) + (A) Composition | 1.729 | 33 | 1.46 | 92 |
| Exam. 6 | Compds. (B) + (E) Composition | 1.725 | 33 | 1.46 | 78 |
| Exam. 7 | Compds. (B) + (F) Composition | 1.722 | 33 | 1.46 | 79 |
| Exam. 8 | Compds. (B) + (G) Composition | 1.728 | 32 | 1.46 | 77 |
| Comp. Exam. 1 | Compd. (H) 89% Composition | 1.701 | 36 | 1.41 | 82 |

Thus, according to the first aspect of this invention a polymerizable composition for an optical resin can provide a transparent resin having excellent optical properties such as a considerably high refractive index, which may contribute to achieving a thinner lens, especially in the field of eyeglasses.

Examples of the second aspect of this invention will be described. The properties relevant to performance of a resin obtained, that is, a refractive index, an Abbe number, and heat resistance were evaluated as described in the above Examples for the first aspect of this invention. Change in tone was rated as follows.

Change rate of tone: A resin was heat ed in the air at 120° C. for 3 hours, and the rate was determined on the basis of the difference between its b* values before and after heating. Each compound (a) was cured in the presence of only a curing catalyst without compound (b). The resin product was heated in the air at 120° C. for 3 hours. The difference between its b* values before and after heating was used as a reference value for tone change.

Change rate of tone={(b* after heating)-(b* before heating)} in the system with Compound (b)/{(b* after heating)-(b* before heating)} in the system without Compound (b)

EXAMPLE 9

N,N-dimethylcyclohexylamine (referred to as DCA) (0.2 g) as a curing catalyst was added to 100 g of Compound (B) as Compound (a) and 5 g of n-propylamine as Compound (b). The mixture was stirred, defoamed 0.4 hours under a reduced pressure, filtered through a 3 μm fluororesin (Teflon®) filter and poured into a mold template consisting of glass molds and a gasket. The mold was gradually warmed from 30° C. to 100° C. and at the temperature the mixture was polymerized for 10 hours. After completion of the polymerization, the mold was gradually cooled and the resin was removed from the mold. The resin was annealed at 100° C. for 2 hours. The resin (lens) was further heated at 120° C. for 3 hours, and then its physical properties were determined. Its physical properties and tone change results are shown in Table 2.

EXAMPLE 10

The procedure as described in Example 9 was repeated, except that n-propylamine as Compound (b) was replaced with 5 g of isopropylamine. The physical properties and the tone change results for the resin are shown in Table 2.

EXAMPLE 11

The procedure as described in Example 9 was repeated, except that n-propylamine as Compound (b) was replaced with 5 g of n-butylamine. The physical properties and the tone change results for the resin are shown in Table 2.

EXAMPLE 12

The procedure as described in Example 9 was repeated, except that n-propylamine as Compound (b) was replaced with 5 g of sec-butylamine. The physical properties and the tone change results for the resin are shown in Table 2.

EXAMPLE 13

The procedure as described in Example 9 was repeated, except that n-propylamine as Compound (b) was replaced with 5 g of tert-butylamine. The physical properties and the tone change results for the resin are shown in Table 2.

EXAMPLE 14

The procedure as described in Example 9 was repeated, except that n-propylamine as Compound (b) was replaced with 5 g of n-hexylamine. The physical properties and the tone change results for the resin are shown in Table 2.

EXAMPLE 15

The procedure as described in Example 9 was repeated, except that n-propylamine as Compound (b) was replaced with 5 g of n-octylamine. The physical properties and the tone change results for the resin are shown in Table 2.

EXAMPLE 16

The procedure as described in Example 9 was repeated, except that n-propylamine as Compound (b) was replaced with 5 g of n-laurylamine. The physical properties and the tone change results for the resin are shown in Table 2.

EXAMPLE 17

The procedure as described in Example 9 was repeated, except that n-propylamine as Compound (b) was replaced with 5 g of methoxyethylamine. The physical properties and the tone change results for the resin are shown in Table 2.

EXAMPLE 18

The procedure as described in Example 9 was repeated, except that n-propylamine as Compound (b) was replaced with 5 g of cyclohexylamine. The physical properties and the tone change results for the resin are shown in Table 2.

EXAMPLE 19

The procedure as described in Example 9 was repeated, except that n-propylamine as Compound (b) was replaced with 3 g of 2-aminoethanol. The physical properties and the tone change results for the resin are shown in Table 2.

EXAMPLE 20

The procedure as described in Example 9 was repeated, except that n-propylamine as Compound (b) was replaced with 5 g of benzylamine. The physical properties and the tone change results for the resin are shown in Table 2.

EXAMPLE 21

The procedure as described in Example 9 was repeated, except that n-propylamine as Compound (b) was replaced with 5 g of β-phenethylamine. The physical properties and the tone change results for the resin are shown in Table 2.

EXAMPLE 22

The procedure as described in Example 9 was repeated, except that n-propylamine as Compound (b) was replaced with 5 g of aniline. The physical properties and the tone change results for the resin are shown in Table 2.

EXAMPLE 23

The procedure as described in Example 9 was repeated, except that n-propylamine as Compound (b) was replaced with 5 g of o-toluidine. The physical properties and the tone change results for the resin are shown in Table 2.

EXAMPLE 24

The procedure as described in Example 9 was repeated, except that n-propylamine as Compound (b) was replaced with 5 g of 2-methylbenzylamine. The physical properties and the tone change results for the resin are shown in Table 2.

EXAMPLE 25

The procedure as described in Example 9 was repeated, except that n-propylamine as Compound (b) was replaced with 5 g of α-naphthylamine. The physical properties and the tone change results for the resin are shown in Table 2.

EXAMPLE 26

The procedure as described in Example 9 was repeated, except that n-propylamine as Compound (b) was replaced with 3 g of ethylenediamine. The physical properties and the tone change results for the resin are shown in Table 2.

EXAMPLE 27

The procedure as described in Example 9 was repeated, except that n-propylamine as Compound (b) was replaced with 3 g of diaminopropane. The physical properties and the tone change results for the resin are shown in Table 2.

EXAMPLE 28

The procedure as described in Example 9 was repeated, except that n-propylamine as Compound (b) was replaced with 3 g of diaminobutane. The physical properties and the tone change results for the resin are shown in Table 2.

EXAMPLE 29

The procedure as described in Example 9 was repeated, except that n-propylamine as Compound (b) was replaced with 3 g of diaminomethylbicycloheptane. The physical properties and the tone change results for the resin are shown in Table 2.

EXAMPLE 30

The procedure as described in Example 9 was repeated, except that n-propylamine as Compound (b) was replaced with 3 g of m-xylylenediamine. The physical properties and the tone change results for the resin are shown in Table 2.

EXAMPLE 31

The procedure as described in Example 9 was repeated, except that n-propylamine as Compound (b) was replaced with 3 g of 1,3-diaminomethylcyclohexylamine. The physical properties and the tone change results for the resin are shown in Table 2.

EXAMPLE 32

The procedure as described in Example 9 was repeated, except that n-propylamine as Compound (b) was replaced with 3 g of naphthalenediamine. The physical properties and the tone change results for the resin are shown in Table 2.

EXAMPLE 33

The procedure as described in Example 9 was repeated, except that n-propylamine as Compound (b) was replaced with 3 g of N,N'-dimethylethylenediamine. The physical properties and the tone change results for the resin are shown in Table 2.

EXAMPLE 34

The procedure as described in Example 9 was repeated, except that n-propylamine as Compound (b) was replaced with 3 g of piperazine. The physical properties and the tone change results for the resin are shown in Table 2.

REFERENCE EXAMPLE 1

Compound (B) (100 g) as Compound (a) was mixed with 5 g of thiophenol as a yellowing inhibitor. To the mixture was added DCA as a curing catalyst and then the mixture was stirred. The subsequent lens molding procedure was conducted as described in Example 9. The physical properties and the tone change results for the resin are shown in Table 3.

REFERENCE EXAMPLE 2

Compound (B) (100 g) as Compound (a) was mixed with 5 g of bis(mercaptoethyl) sulfide as a yellowing inhibitor. To the mixture was added DCA as a curing catalyst and then the mixture was stirred. The subsequent lens molding procedure was conducted as described in Example 9. The physical properties and the tone change results for the resin are shown in Table 3.

TABLE 2

| Ex. No. | Composition (a) | Composition (b) | Amino/Thioepoxy | Change rate of tone | Refractive Index (nd) | Abbe No. (vd) | Heat resistance (Tg, °C.) |
|---|---|---|---|---|---|---|---|
| 9  | Compd. (B) | n-Propylamine | 0.089 | 0.500 | 1.723 | 34 | 81 |
| 10 | Compd. (B) | Isopropylamine | 0.089 | 0.516 | 1.720 | 34 | 78 |
| 11 | Compd. (B) | n-Butylamine | 0.072 | 0.500 | 1.722 | 34 | 79 |
| 12 | Compd. (B) | sec-Butylamine | 0.072 | 0.548 | 1.722 | 34 | 79 |
| 13 | Compd. (B) | tert-Butylamine | 0.072 | 0.500 | 1.723 | 34 | 80 |
| 14 | Compd. (B) | n-Hexylamine | 0.052 | 0.468 | 1.722 | 34 | 79 |
| 15 | Compd. (B) | n-Octylamine | 0.041 | 0.435 | 1.719 | 34 | 78 |
| 16 | Compd. (B) | n-Laurylamine | 0.028 | 0.468 | 1.720 | 34 | 77 |
| 17 | Compd. (B) | Methoxyethylamine | 0.070 | 0.532 | 1.722 | 33 | 79 |
| 18 | Compd. (B) | Cyclohexylamine | 0.053 | 0.532 | 1.718 | 34 | 78 |
| 19 | Compd. (B) | 2-Aminoethanol | 0.043 | 0.468 | 1.723 | 33 | 80 |
| 20 | Compd. (B) | Benzylamine | 0.049 | 0.484 | 1.727 | 33 | 78 |
| 21 | Compd. (B) | β-Phenethylamine | 0.043 | 0.532 | 1.727 | 33 | 79 |
| 22 | Compd. (B) | Aniline | 0.056 | 0.581 | 1.729 | 33 | 79 |
| 23 | Compd. (B) | o-Toluidine | 0.049 | 0.581 | 1.728 | 33 | 78 |
| 24 | Compd. (B) | 2-Methylbenzylamine | 0.043 | 0.565 | 1.728 | 33 | 78 |
| 25 | Compd. (B) | α-Naphthylamine | 0.037 | 0.887 | 1.725 | 33 | 78 |
| 26 | Compd. (B) | Ethylenediamine | 0.105 | 0.532 | 1.724 | 33 | 77 |
| 27 | Compd. (B) | Diaminopropane | 0.085 | 0.532 | 1.725 | 33 | 77 |
| 28 | Compd. (B) | Diaminobutane | 0.072 | 0.548 | 1.724 | 33 | 77 |
| 29 | Compd. (B) | Diaminomethyl-bicycloheptane | 0.048 | 0.500 | 1.720 | 34 | 81 |
| 30 | Compd. (B) | m-Xylylenediamine | 0.046 | 0.565 | 1.728 | 33 | 80 |
| 31 | Compd. (B) | 1,3-Diaminomethyl-cyclohexylamine | 0.044 | 0.484 | 1.722 | 33 | 79 |
| 32 | Compd. (B) | Naphthalenediamine | 0.040 | 0.935 | 1.726 | 33 | 79 |
| 33 | Compd. (B) | N,N'-dimethylethylenediamine | 0.071 | 0.532 | 1.722 | 33 | 83 |
| 34 | Compd. (B) | Piperazine | 0.073 | 0.323 | 1.732 | 33 | 96 |

TABLE 3

| Ref. Ex. No. | Composition (a) | Yellowing inhibitor | Curing catalyst | Functional group/Thioepoxy group | Change rate of tone | Refractive Index (nd) | Abbe No. (vd) | Heat resistance (Tg, °C.) |
|---|---|---|---|---|---|---|---|---|
| 1 | Compd. (B) | Thiophenol | DCA | 0.048 | 0.581 | 1.732 | 33 | 72 |
| 2 | Compd. (B) | Bis(mercaptoethyl)-sulfide | DCA | 0.068 | 0.516 | 1.733 | 33 | 74 |

What is claimed is:

1. A polymerizable composition comprising a (thio)epoxy compound having at least one intramolecular disulfide bond and 4,8-, 4,7- or 5,7-dimercaptomethyl-1,11-dimercapto-3,6,9-trithiaundecane.

2. A polymerizable composition as claimed in claim 1 where the (thio)epoxy compound having at least one intramolecular disulfide bond is represented by formula (1):

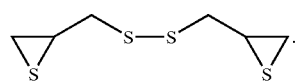

3. A transparent resin obtained by polymerizing and curing the polymerizable composition as claimed in claim 1.

4. A transparent resin obtained by polymerizing and curing the polymerizable composition as claimed in claim 2.

5. A transparent resin as claimed in claim 3, wherein the transparent resin is a transparent optical material.

6. A transparent resin as claimed in claim 4, wherein the transparent resin is a transparent optical material.

7. A transparent resin as claimed in claim 5, wherein the transparent optical material is a plastic lens.

8. A transparent resin as claimed in claim 6, wherein the transparent optical material is a plastic lens.

9. A method for preparing a transparent resin which comprises a step of casting polymerization of the polymerizable composition as claimed in claim 1.

10. A method for preparing a transparent resin which comprises a step of casting polymerization of the polymerizable composition as claimed in claim 2.

* * * * *